United States Patent
Rowe et al.

(10) Patent No.: US 6,234,990 B1
(45) Date of Patent: *May 22, 2001

(54) ULTRASOUND ENHANCEMENT OF TRANSDERMAL TRANSPORT

(75) Inventors: Stephen Rowe, Wellesley, MA (US); Joseph Kost, Omer (IL); Samir S. Mitragotri, Cambridge, MA (US); Michael Pishko, Bryan, TX (US); Matthew Davis, Boston, MA (US)

(73) Assignee: Sontra Medical, Inc., Cambridge, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/885,931

(22) Filed: Jun. 30, 1997

Related U.S. Application Data

(60) Provisional application No. 60/034,657, filed on Jan. 8, 1997, provisional application No. 60/033,996, filed on Jan. 3, 1997, provisional application No. 60/033,047, filed on Dec. 11, 1996, provisional application No. 60/024,639, filed on Aug. 22, 1996, provisional application No. 60/023,636, filed on Aug. 9, 1996, provisional application No. 60/022,925, filed on Aug. 1, 1996, provisional application No. 60/022,923, filed on Aug. 1, 1996, and provisional application No. 60/020,953, filed on Jun. 28, 1996.

(51) Int. Cl.[7] .................................................. A61B 17/20
(52) U.S. Cl. .............................................................. 604/22
(58) Field of Search ........................ 601/2, 17; 607/154; 604/20, 22, 49, 66, 289, 290

(56) References Cited

U.S. PATENT DOCUMENTS

| | | |
|---|---|---|
| 3,551,554 | 12/1970 | Herschler . |
| 3,711,602 | 1/1973 | Herschler . |
| 3,711,606 | 1/1973 | Herschler . |
| 4,002,221 | 1/1977 | Buchalter . |
| 4,127,125 | 11/1978 | Takemoto et al. . |

(List continued on next page.)

FOREIGN PATENT DOCUMENTS

| | | |
|---|---|---|
| 27 56 460A 1 | 6/1979 | (DE) . |
| 43738 B1 | 10/1985 | (EP) . |
| 386408 A2 | 5/1990 | (EP) . |
| 495 531 A1 | 7/1992 | (EP) . |
| 612525 A1 | 8/1994 | (EP) . |

(List continued on next page.)

OTHER PUBLICATIONS

Apfel, R. E., "Possibility of Microcavitation from Diagnostic Ultrasound," *IEEE Trans. Ultrason. Ferroelectrics Freq. Control* UFFC–33:139–142 (1986).

(List continued on next page.)

*Primary Examiner*—Sharon Kennedy
(74) *Attorney, Agent, or Firm*—Arnall Golden & Gregory, LLP

(57) ABSTRACT

Methods and devices for application of ultrasound to a small area of skin for enhancing transdermal transport. An ultrasound beam having a first focal diameter is channelled into a beam having a second, smaller diameter without substantial loss of energy. Higher energy ultrasound can be used while causing less pain. Alternatively, ultrasound energy is applied through a vibrating element positioned just contacting, above or extending into the skin. Use of the element facilitates extraction of analyte and may enhance drug delivery. A two step noninvasive method involves application of ultrasound to increase skin permeability and removal of ultrasound followed by transdermal transport that can be further enhanced using a physical enhancer.

15 Claims, 6 Drawing Sheets

U.S. PATENT DOCUMENTS

| | | |
|---|---|---|
| 4,144,646 | 3/1979 | Takemoto et al. . |
| 4,176,664 | 12/1979 | Kalish . |
| 4,249,531 | 2/1981 | Hiller et al. . |
| 4,280,494 | 7/1981 | Cosgrove et al. . |
| 4,309,989 | 1/1982 | Fahim . |
| 4,372,296 | 2/1983 | Fahim . |
| 4,537,776 | 8/1985 | Cooper . |
| 4,557,943 | 12/1985 | Rosler et al. . |
| 4,563,184 | 1/1986 | Korol . |
| 4,595,011 | 6/1986 | Philips . |
| 4,646,725 | 3/1987 | Moasset . |
| 4,698,058 | 10/1987 | Greenfeld et al. . |
| 4,732,153 | 3/1988 | Philips . |
| 4,767,402 * | 8/1988 | Kost et al. ............................ 604/20 |
| 4,780,212 | 10/1988 | Kost et al. . |
| 4,787,070 * | 11/1988 | Suzuki et al. ........................... 601/2 |
| 4,787,888 | 11/1988 | Fox . |
| 4,820,720 | 4/1989 | Sanders et al. . |
| 4,821,733 | 4/1989 | Peck . |
| 4,821,740 | 4/1989 | Tachibana et al. . |
| 4,834,978 | 5/1989 | Nuwayser . |
| 4,855,298 | 8/1989 | Yamada et al. . |
| 4,860,058 | 8/1989 | Kobayashi et al. . |
| 4,863,970 | 9/1989 | Patel et al. . |
| 4,953,565 | 9/1990 | Tachibana et al. . |
| 5,006,342 | 4/1991 | Cleary et al. . |
| 5,007,438 | 4/1991 | Tachibana et al. . |
| 5,016,615 * | 5/1991 | Driller et al. ......................... 604/20 |
| 5,076,273 | 12/1991 | Schoendorfer et al. . |
| 5,078,144 | 1/1992 | Sekino . |
| 5,115,805 * | 5/1992 | Bommannan et al. ................ 604/20 |
| 5,139,023 | 8/1992 | Stanley et al. . |
| 5,140,985 | 8/1992 | Schroder et al. . |
| 5,171,215 * | 12/1992 | Flanagan ................................ 604/22 |
| 5,197,946 | 3/1993 | Tachibana . |
| 5,230,334 * | 7/1993 | Klopotek ................................. 606/1 |
| 5,231,975 | 8/1993 | Bommannan et al. . |
| 5,267,985 | 12/1993 | Shimada et al. . |
| 5,315,998 | 5/1994 | Tachibana et al. . |
| 5,323,769 | 6/1994 | Bommannan et al. . |
| 5,386,837 | 2/1995 | Sterzer . |
| 5,401,237 | 3/1995 | Tachibana et al. . |
| 5,405,614 | 4/1995 | D'Angelo et al. . |
| 5,415,629 | 5/1995 | Henley . |
| 5,421,816 * | 6/1995 | Lipkovker ............................. 604/20 |
| 5,443,080 | 8/1995 | D'Angelo . |
| 5,445,611 * | 8/1995 | Eppstein et al. ...................... 604/49 |
| 5,458,140 | 10/1995 | Eppstein et al. . |
| 5,617,851 | 4/1997 | Lipkovker . |
| 5,618,275 * | 4/1997 | Bock ..................................... 604/22 |
| 5,626,554 * | 5/1997 | Ryaby et al. ........................... 601/2 |
| 5,636,632 * | 6/1997 | Bommannan et al. ............... 604/22 |
| 5,656,016 * | 8/1997 | Ogden ................................... 604/22 |

FOREIGN PATENT DOCUMENTS

| | | |
|---|---|---|
| 1 577 551 | 2/1976 | (GB) . |
| 2153223 | 8/1985 | (GB) . |
| 3-170172 | 7/1991 | (JP) . |
| 445433 | 11/1974 | (SU) . |
| 556805 | 6/1977 | (SU) . |
| 591186 | 1/1978 | (SU) . |
| 0910157 | 2/1978 | (SU) . |
| 506421 | 2/1978 | (SU) . |
| WO 88/00001 | 1/1988 | (WO) . |
| WO 90/01971 | 3/1990 | (WO) . |
| WO 90/15568 | 12/1990 | (WO) . |
| WO 91/12772 | 9/1991 | (WO) . |
| WO 93/20745 | 10/1993 | (WO) . |
| WO 94/08655 | 4/1994 | (WO) . |
| WO 97/04832 | 2/1997 | (WO) . |

OTHER PUBLICATIONS

Aungst, et al., "Contributions of Drug Solubilization, Partitioning, Barrier Disruption, and Solvent Permeation to the Enhancement of Skin Permeation of Various Compounds with Fatty Acids and Amines," *Pharm. Res.* 7:712–718 (1990).

Barry, "Mode of Action of Penetration Enhancers in Human Skin," *J. Controlled Rel.* 6:85–97 (1987).

Bommer, et al., "Subcutaneous Erythropoeitin," *Lancet* 406 (1988).

Burnette, R. R., "Iontophoresis," *Transdermal Drug Delivery Developmental Issues and Research Initiatives* (Hadgraft and Guy, Editors, Marcel Dekker, 247–291, 1989).

Cleary, Gary W., "Transdermal Controlled Release Systems," *Medical Applications of Controlled Release* (Langer and Wise, Editors, CRC Press 203–251, 1984).

Clegg and Vaz, "Translational diffusion of proteins and lipids in artificial lipid bilayer membranes. A comparison of experiment with theory," *Progress in Protein–Lipid Interactions* Watts, ed. (Elsvier, NY 1985) Chapter 5:173–229.

Davis, J.,et al., "Characterization of Recombinant Human Erythropoietin Produced in Chinese Hamster Ovary Cells," *Biochemistry* 26:2633–2638 (1987).

Ebert, et al., "Transbuccal Absorption of Diclofenac Sodium in a Dog Model," *Controlled Release Technology Pharmaceutial Applications* (Lee, et al. Editors, American Chemical Society)310–321 (1987).

Eggerth, et al., "Evaluation of Hamster Cheek Pouch as a Model for Buccal Absorption," *Proceed. Intern. Symp. Rel. Bioact. Mater.,*(Controlled Release Society, Inc.) 14:180–181 (1987).

D'Emanuele, et al., "An Investigation of the Effects of Ultrasound on Degradable Polyanhydride Matrices," *Macromolecules* 25:511–515 (1992).

Elias, "The Microscopic Structure of the Epidermis and Its Derivatives," *Percutaneous Absorption: Mechanisms–Methodology–Drag Delivery* (Bronaugh, R. L., Maibach, H., Editors, Marcel Dekker, New York,) 1–12 (1989).

Egorov, E.A. et al., "Use of the Variants of the Pharmacophysical Influence in Ophthalmology", 102 Ophthalmology Journal #2 (1992).

Eppstein, D.A. et al., "Applications of Liposome Formulations for Antimicrobial/Antiviral Therapy" Liposomes as Drug Carriers 311, 315 (G. Gregoriadis ed. 1988).

Eppstein, D.A., "Medical Utility of Inteferons: Approaches to Increasong Therapeutic Efficacy" 7 Pharmacy International 195–198 (1986).

Eppstein, D.A. et al., "Alternative Delivery Systems for Peptides and Proteins as Drugs" 5 CRC Reviews in Therapeutic Drug Carrier Systems 99, 125 (1988).

Flynn, G. L., "Mechanism of Percutaneous Absorption from Physicochemical Evidence," *Percutaneous Absorption: Mechanisms–Methodology–Drug Delivery* (Bronaugh, R. L., Maibach, H., Editors, Marcel Dekker, New York) 27–51 (1989).

Gaertner, W., "Frequency Dependence of Ultrasonice Cavitation," *J. Acoust. Soc. Am.* 26:977–980 (1954).

Ghanem et al., "The effects of ethanol on the transport of lipophilic and polar permeants across hairless mouse skin: Methods/validation of a novel approach," *Int. J. Pharm.* 78:137–156 (1992).

Grups and Frohmuller, "Cyclic Interferon Gamma Treatment of Patients with Metastatic Renal Carcinoma," *J. Med.* 64(3):218–220 (1989).

Junginger, et al., "Visualization of Drug Transport Across Human Skin and the Influence of Penetration Enhancers," *"Drug Permeation Enhancement"* (Hsieh, D.S., Editors, Marcel Dekker, Inc. New York) 59–89 (1994).

Kasting, et al., "Prodrugs for Dermal Delivery: Solubility, Molecular Size, and Functional Group Effects," "Prodrugs: Topical and Ocular Delivery" Sloan, ed. (Marcel Dekker, NY 1992) 117–161.

Kost and Langer, "Ultrasound–Mediated Transdermal Drug Delivery," *Topical Drug Bioavailability Bioequivalence and Penetration* (Maibach, H. I., Shah, V. P., Editors, Plenum Press, New York) 91–104 (1993).

Kost, et al., "Ultrasound Effect on Transdermal Drug Delivery," (Ben Gurion University Dept. of Chem. Engineering, Beer Sheva Israel) (MIT, Dept. of Applied Biological Sciences, Cambridge, MA) CRS Aug. 1986.

Lee, V. H. L., et al., "Protease Inhibition as an Additional Mechanism for the Nasal Absorption Enhancement Effect of Sodim Taurodihydrofusidate," *Proceed. Intern. Symp. Control. Rel. Bioact. Mater* 14:55–56 (1987).

Lee, V. H. L., et al., "Nasal Peptide and Protein Absorption Promotors: Aminopeptidase Inhibition as a Predictor of Absorption Enhancement Potency of Bile Salts," *Proceed. Intern. Symp. Control. Rel. Bioact. Mater* 14:53–54 (1987).

Levy, et al., "Effect of Ultrasound on Transdermal Drug Delivery to Rats and Guinea Pigs," *J. Clin. Invest.* 83:2074–2078 (1989).

Liu, et al., "Cotransport of Estradiol and Ethanol Through Human Skin In Vitro: Understanding the Permeant/Enhancer Flux Relationship," *Pharmaceutical Research* 8:938–944 (1991).

Liu, et al., "Experimental Approach To Elucidate the Mechanism of Ultrasound–Enhanced Polymer Erosion and Release of Incorporated Substances," *Macromolecules* 25:123–128 (1992).

Loshilov, V.I. et al., "Research of the Technological Process of Ultrasound Treatment of Infected Wounds" (1976).

Machluf and Kost, "Ultrasonically enhanced transdermal drug delivery. Experimental approaches to elucidate the mechanism," *J. Biomater. Sci. Polymer Edn.* 5:147–156 (1993).

Mak, et al., "Oleic Acid Concentration and Effect in Human Stratum Corneum: Non–Invasive Determination by Attenuated Total Reflectance Infrared Spectroscopy In Vivo," *J. Controlled Rel.* 12:67–75 (1990).

Mitragotri, et al., "Ultrasound–Mediated Transdermal Protein Delivery," *Science* 269:850–853 (1995).

Mitragotri, et al., "A Mechanistic Study of Ultrasonically–Enhanced Transdermal Drug Delivery," *J. Pharm. Sci.* 84:697–706 (1995).

Morimoto, Y., et al., "Prediction of Skin Permeability of Drugs: Comparison of Human and Hairless Rat Skin," *J. Pharm. Pharmacol.* 44:634–639 (1991).

Nagai and Konishi, "Buccaal/Gingival Drug Delivery Systems," *Journal of Controlled Release* (Elsevier Science Publishers B.V., Amsterdam) 6:353–360 (1987).

Newman, J., et al., "Hydrocortisone Phonophoresis," *J. Am. Pod. Med. Assoc.* 82:432–435 (1992).

Olanoff and Gibson, "Method to Enhance Intranasal Peptide Delivery," *Controlled Release Technology Pharmaceutical Application* (Lee, et al. Editors, American Chemical Society) 301–309 (1987).

Ongpipattanankul, et al., "Evidence that Oleic Acid Exists in a Separate Phase Within Stratum Corneum Lipids," *Pharm. Res.* 8:350–354 (1991).

Parkin, et al., "Atopic manifestations in the acquired immune deficiency syndrome: response to recombinant interferon gamma," *Br. Med. J.,* 294:1185–1186 (1987).

Pishko, et al., "Amperometric Glucose Microelectrodes Prepared through Immobilization of Glucose Oxidase in Redox Hydrogels," *Anal. Chem.* 63:2268–2272 (1991).

Potts and Guy, "Predicting Skin Permeability," *Pharm. Res.* 9:663–669 (1992).

Prausnitz, et al., "Electroporation of mammalian skin: A mechanism to enhance transdermal drug delivery," *Proc. Natl. Acad. Sci.USA* 90:10504–10508 (1993).

Quillen, W.S., "Phonophoresis: A Review of the Literature and Technique," *Athl. Train.* 15:109–110 (1980).

Robinson & Lee, "Influence of Drug Properties on Design," *Controlled Drug Delivery* 42–43.

Rosell, J., et al., "Skin Impedance From 1 Hz to 1 MHz," *IEEE Trans. Biomed. Eng.* 35:649–651 (1988).

Skauen, et al., "Phonophoresis," *Int. J. Pharm.* 20:235–245 (1984).

Tamada, et al., *Proceed. Intern. Symp. Control. Rel. Bioact. Mater.* 22, 129–130 (1995).

Tocanne, et al., "Lipid lateral diffusion and membrane organization," *FEB* 257:10–16 (1989).

Tyle and Agrawala, "Drug Delivery by Phonophoresis," *Pharm. Res.* 6:355–361 (1989).

Ulashik, V.S. et al., Ultrasound Therapy (Minsk, Belarus 1983).

Walker and Hadgraft, "Oleic Acid–a Membrane 'Fluidiser'or Fluid within the Membrane, "Int. J. Pharm. 71:R1–R4 (1991).

Walmsley, "Applications of Ultrasound in Dentistry," *Ultrasound in Med. and Biol.* 14:7–14 (1988).

Walters, K. A., "Penetration Enhancers and Their Use in Transdermal Therapeutic Systems," *Transdermal Drug Delivery: Developmental Issues and Research Initiatives,* 197–246 (Hadgraft J., Guy, R.H., Editors, Marcel Dekker, 1989).

Wester and Mailbach, "Animal Models for Percutaneous Absorption," *Topical Drug Bioavailability Bioequivalence and Penetration* (Shah and Maibach, Editors, Plenum Press, New York) 333–349, (1993).

Wheatley, et al., "Use of Ussing Chamber for Investigation of Drug Delivery Across Viable Nasal Tissue Membranes," *Proceed. Intern. Symp. Control. Rel. Bioact. Mater.* (Controlled Release Society, Inc. 14:26–27 (1987).

Williams, et al., "On the non–Gaussian distribution of human skin permeabilities," *Int. J. Pharm.* 86:69–77 (1992).

Wilschut, et al., "Estimating Skin Permeation. The Validation of Five Mathematical Skin Permeation Models," *Chemosphere* 30:1275–1296 (1995).

* cited by examiner

ULTRASOUND ENHANCEMENT OF TRANSDERMAL TRANSPORT

This application claims priority from U.S. provisional patent application Ser. No. 60/020,953 filed Jun. 28, 1996, Ser. No. 60/022,925 filed Aug. 1, 1996, Ser. No. 60/022,923 filed Aug. 1, 1996, Ser. No. 60/023,636 filed Aug. 9, 1996, Ser. No. 60/034,657 filed Jan. 8, 1997, Ser. No. 60/024,639 filed Aug. 22, 1996, Ser. No. 60/033,047 filed Dec. 11, 1996 and Ser. No. 60/033,996 filed Jan. 3, 1997.

BACKGROUND OF THE INVENTION

The present invention generally relates to improved methods and devices for transdermal transport using ultrasound. More specifically, methods and devices are provided to channel or focus an ultrasound beam so that it is applied to a small area of skin and can enhance drug delivery and analyte collection. Methods and devices are provided to localize the ultrasound energy onto a vibrating element which applies the ultrasound energy to a small area of the skin.

Drugs are routinely administered orally or by injection. The effectiveness of most drugs relies on achieving a certain concentration in the bloodstream. Many drugs exhibit undesirable behaviors that are specifically related to a particular route of administration. For example, drugs may be degraded in the gastrointestinal (GI) tract by the low gastric pH, local enzymes, or interaction with food or drink in the stomach. The drug or disease itself may forestall or compromise drug absorption because of vomiting or diarrhea. If a drug entity survives its trip through the GI tract, it may face rapid metabolism to pharmacologically inactive forms by the liver, the first pass effect.

Transdermal drug delivery (TDD) offers several advantages over traditional delivery methods including injections and oral delivery. When compared to oral delivery, TDD avoids gastrointestinal drug metabolism, reduces first-pass effects, and provides sustained release of drugs for up to seven days, as reported by Elias, in *Percutaneous Absorption: Mechanisms-Methodology-Drug Delivery,* Bronaugh, R. L., Maibach, H. 1. (Ed), pp 1–12, Marcel Dekker, New York, 1989.

The skin is a complex structure. There are at least four distinct layers of tissue: the nonviable epidermis (stratum corneum, SC), the viable epidermis, the viable dermis, and the subcutaneous connective tissue. Located within these layers are the skin's circulatory system, the arterial plexus, and appendages, including hair follicles, sebaceous glands, and sweat glands. The circulatory system lies in the dermis and tissues below the dermis. The capillaries do not actually enter the epidermal tissue but come within 150 to 200 microns of the outer surface of the skin.

The word "transdermal" is used herein as a generic term. However, in actuality, transport of drugs occurs only across the epidermis where the drug gets absorbed in the blood capillaries. In comparison to injections, TDD can reduce or eliminate the associated pain and the possibility of infection. Theoretically, the transdermal route of drug administration could be advantageous in the delivery of many therapeutic drugs, including proteins, because many drugs, including proteins, are susceptible to gastrointestinal degradation and exhibit poor gastrointestinal uptake, proteins such as interferons are cleared rapidly from the blood and need to be delivered at a sustained rate in order to maintain their blood concentration at a high value, and transdermal devices are easier to use than injections.

In spite of these advantages, very few drugs and no proteins or peptides are currently administered transdermally for clinical applications because of the low skin permeability to drugs. This low permeability is attributed to the stratum corneum (SC), the outermost skin layer which consists of flat, dead cells filled with keratin fibers (keratinocytes) surrounded by lipid bilayers. The highly-ordered structure of the lipid bilayers confers an impermeable character to the SC (Flynn, G. L., in *Percutaneous Absorption: Mechanisms-Methodology-Drug Delivery.;* Bronough, R. L., Maibach, H. I. (Ed), pages 27–53, Marcel Dekker, New York, 1989). Several methods have been proposed to enhance transdermal drug transport, including the use of chemical enhancers, i.e. the use of chemicals to either modify the skin structure or to increase the drug concentration in a transdermal patch (Burnette, R. R., in *Developmental Issues and Research Initiatives;* Hadgraft J., G., R. H., Eds., Marcel Dekker: 1989; pp. 247–288; Junginger, et al. in *Drug Permeation Enhancement;* Hsieh, D. S., Eds., pp. 59–90; Marcel Dekker, Inc. New York 1994) and the use of applications of electric fields to create transient transport pathways [electroporation] or to increase the mobility of charged drugs through the skin [iontophoresis] (Prausnitz *Proc. Natl. Acad. Sci. USA* 90, 10504–10508 (1993); Walters, K. A., in *Transdermal Drug Delivery: Developmental Issues and Research Initiatives,* Ed. Hadgraft J., Guy, R. H., Marcel Dekker, 1989). Another approach that has been explored is the application of ultrasound [sonophoresis].

Ultrasound has been shown to enhance transdermal transport of low-molecular weight drugs (molecular weight less than 500) across human skin, a phenomenon referred to as sonophoresis (Levy, J. Clin. Invest. 1989, 83, 2974–2078; Kost and Langer in "*Topical Drug Bioavailability, Bioequivalence, and Penetration*"; pp. 91–103, Shah V. P., M. H. I., Eds. (Plenum: New York, 1993); Frideman, R. M., "*Interferons: A Primer*", Academic Press, New York, 1981). Although a variety of ultrasound conditions have been used for sonophoresis, the most commonly used conditions correspond to therapeutic ultrasound (frequency in the range of between one MHz and three MHz, and intensity in the range of between above zero and two W/cm$^2$) (U.S. Pat. No. 4,767,402 to Kost, et al.). It is a common observation that the typical enhancement induced by therapeutic ultrasound is less than ten-fold. In many cases, no enhancement of transdermal drug transport has been observed upon ultrasound application. Accordingly, a better selection of ultrasound techniques is needed to induce a higher enhancement of transdermal drug transport by sonophoresis.

Application of low-frequency (between approximately 20 and 200 kHz) ultrasound can dramatically enhance transdermal transport of drugs, as described in PCT/US96/12244 by Massachusetts Institute of Technology. Transdermal transport enhancement induced by low-frequency ultrasound was found to be as much as 1000-fold higher than that induced by therapeutic ultrasound. Another advantage of low-frequency sonophoresis as compared to therapeutic ultrasound is that the former can induce transdermal transport of drugs which do not passively permeate across the skin.

There is a major medical need to extract analytes through the skin, such as in diabetics where it is desirable to measure blood glucose several times per day in order to optimize insulin treatment and thereby reduce the severe long-term complications of the disease. Currently, diabetics do this by pricking the highly vascularized fingertips with a lancet to perforate the skin, then milking the skin with manual pressure to produce a drop of blood, which is then assayed for glucose using a disposable diagnostic strip and a meter into which this strip fits. This method of glucose measurement has the major disadvantage that it is painful, so diabetics do not like to obtain a glucose measurement as often as is medically indicated.

Therefore, many groups are working on non-invasive and less invasive means to measure glucose, such as micro lancets that are very small in diameter, very sharp, and penetrate only to the interstitium (not to the blood vessels of the dermis). A small sample, from about 0.1 to two $\mu l$, of interstitial fluid is obtained through capillary forces for glucose measurements. Other groups have used a laser to breach the integrity of the stratum corneum and thereby make it possible for blood or interstitial fluid to diffuse out of such a hole or to be obtained through such a hole using pneumatic force (suction) or other techniques. An example of such a laser based sampling device is disclosed in U.S. Pat. No. 5,165,418 to Tankovich and WPI ACC No: 94-167045/20 by Budnik (assigned to Venisect, Inc.).

A problem with methods that penetrate the skin to obtain interstitial fluid is that interstitial fluid occurs in the body in a gel like form with little free fluid and in fact there is even negative pressure that limits the amount of free interstitial fluid that can be obtained. When a very small hole is made in the skin, penetrating to a depth such that interstitial fluid is available, it takes a great deal of mechanical force (milking, vacuum, or other force) to obtain the quantity of blood used in a glucose meter.

It would be of significant utility to be able to obtain a sample of blood or interstitial fluid more quickly, using an easier procedure, and noninvasively.

SUMMARY OF THE INVENTION

The methods and devices described herein channel or focus an ultrasound beam onto a small area of skin. In some embodiments, methods and devices utilizing a chamber and ultrasound probe disclosed herein can be used to noninvasively extract analyte and deliver drugs. This provides many advantages, including the ability to create a small puncture or localized erosion of the skin tissue, without a large degree of concomitant pain. The number of pain receptors within the ultrasound application site decreases as the application area decreases. Thus, the application of ultrasound to a very small area will produce less sensation and will allow ultrasound and/or its local effects to be administered at higher intensities with little pain or discomfort. Channeling of ultrasound geometrically is one way to apply ultrasound to a small area. The oscillation of a small element near or in contact with the surface of the skin is another way to apply ultrasound to a small area. Large forces can be produced locally, resulting in cavitation, mechanical oscillations in the skin itself, and large localized shearing forces near the surface of the skin. The element can also produce acoustic streaming, which refers to the large convective flows produced by ultrasound. This appears to aid in obtaining a sample of blood or interstitial fluid without having to "milk" the puncture site. Ultrasound transducers are known to rapidly heat under continuous operation, reaching temperatures that can cause skin damage. Heat damage to the skin can be minimized by using a transducer that is located away from the skin to oscillate a small element near the skin. In the case of analyte extraction, compounds present on the surface of and/or in the skin can contaminate the extracted sample. The level of contamination increases as skin surface area increases. Surface contamination can be minimized by minimizing the surface area of ultrasound application. Thus, skin permeability can be increased locally and transiently through the use of the methods and devices described herein, for either drug delivery or measurement of analyte.

DETAILED DESCRIPTION OF THE INVENTION

Figure 1:
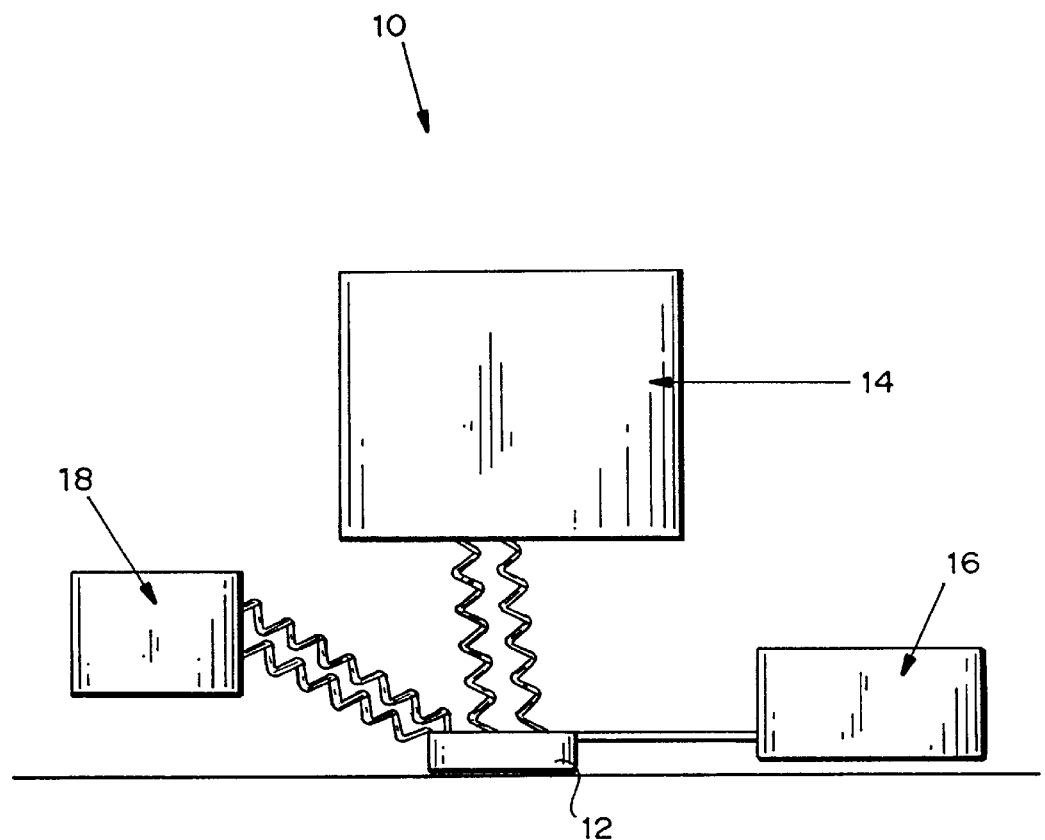
FIG. 1 is a schematic of an ultrasound focusing device including an ultrasound channeling chamber.

Ultrasound is defined as sound at a frequency of higher than about 20 kHz and 10 MHz, with intensities of between greater than zero and three $W/cm^2$. Ultrasound is preferably administered at frequencies of less than or equal to about 2.5 MHz to induce cavitation of the skin to enhance transport. Exposures are typically for between 20 seconds and 10 minutes, continuously, but may be shorter and/or pulsed. It should be understood that although the normal lower range of ultrasound is 20 kHz, one could achieve comparable results by varying the frequency to less than 20 kHz, that is, into the sound region down to about one kHz. The intensity should not be so high as to raise the skin temperature more than about one to two degrees Centigrade.

As used herein, sonophoresis is the application of ultrasound to the skin. "Low frequency" sonophoresis is ultrasound at a frequency that is less than one MHz, more typically in the range of 20 to 100 kHz, which is applied continuously or, preferably, in pulses, for example, 100 to 500 msec pulses every second at intensities in the range of between above zero and one $W/cm^2$, more typically between 12.5 $mW/cm^2$ and 225 $mW/cm^2$.

Chemical enhancers include lipid bilayer disrupting agents and solubility enhancers. Chemical enhancers have been found to increase drug transport by different mechanisms. Chemicals which enhance permeability through lipids are known and commercially available. For example, ethanol has been found to increase the solubility of drugs up to 10,000-fold and yield a 140-fold flux increase of estradiol, while unsaturated fatty acids have been shown to increase the fluidity of lipid bilayers. Examples of fatty acids which disrupt lipid bilayer include linoleic acid, capric acid, lauric acid, and neodecanoic acid, which can be in a solvent such as ethanol or propylene glycol. Suitable solvents include water; diols, such as propylene glycol and glycerol; monoalcohols, such as ethanol, propanol, and higher alcohols; DMSO; dimethylformamide; N,N-dimethylacetamide; 2-pyrrolidone; N-(2-hydroxyethyl) pyrrolidone, N-methylpyrrolidone, 1-dodecylazacycloheptan-2-one and other n-substituted-alkyl-azacycloalkyl-2-ones and other n-substituted-alkyl-azacycloalkyl-2-ones (azones).

Other chemical enhancers, not necessarily associated with binary systems, include dimethylsulfoxide (DMSO) or aqueous solutions of DMSO such as those described in U.S. Pat. No. 3,551,554 to Herschler; U.S. Pat. No. 3,711,602 to Herschler; and U.S. Pat. No. 3,711,606 to Herschler, and the azones (n-substituted-alkyl-azacycloalkyl-2-ones) such as noted in U.S. Pat. No. 4,557,943 to Coope Physical enhancers, as used herein, include suction, osmotic pressure gradient, iontophoresis, electroporation, magnetic fields, and mechanical pressure.

Drugs to be administered include a variety of bioactive agents, including proteins and peptides. Specific examples include insulin, erythropoietin, and interferon. Other materials, including nucleic acid molecules such as antisense and genes encoding therapeutic proteins, synthetic organic and inorganic molecules including antiinflammatories, antivirals, antifungals, antibiotics, local anesthetics, and saccharides and polysaccharides, can also be administered. The drug will typically be administered in an appropriate pharmaceutically acceptable carrier having an absorption coefficient similar to water, such as an aqueous gel, ointment, lotion, or suspension. Alternatively, a transdermal patch can be used as a carrier.

A variety of analytes are routinely measured in the blood, interstitial fluid and/or lymph. Examples of typical analytes that can be measured include blood sugar (glucose), cholesterol, bilirubin, creatine, vitamin K or other clotting factors, uric acid, carcinoembryonic antigen or other tumor antigens, and various reproductive hormones such as those associated with ovulation or pregnancy.

The methods and devices disclosed herein may achieve greater transdermal transport by inducing cavitation either inside or outside of the skin. Cavitation is the growth and oscillations of air bubbles present in fluids and air pockets present in the keratinocytes of the SC. Application of low-frequency ultrasound appears to induce cavitation inside as well as outside the skin and disorganize the SC lipid bilayers thereby enhancing transdermal transport. In addition, oscillations of cavitation bubbles may result in significant water penetration into the disordered lipid regions and may cause the formation of aqueous channels through the intercellular lipids of the SC. This allows transport of permeants across the disordered lipid domains, then across keratinocytes and the entire SC. This transport pathway may result in an enhanced transdermal transport as compared to passive transport because the diffusion coefficients of permeants through water, which is likely to primarily occupy the channels generated by ultrasound, are up to 1000-fold higher than those through the ordered lipid bilayers, and the transport path length of these aqueous channels may be much shorter (by a factor of up to 25) than that through the tortuous intercellular lipids in the case of passive transport.

Ultrasound Channeling or Focusing

Transdermal transport enhancement induced by ultrasound increases with increasing ultrasound pressure amplitude. However, application of high ultrasound pressure amplitudes is prohibited by the discomfort associated with it. The extent of discomfort induced by ultrasound increases with increasing application area, probably due to exposure of more pain receptors to ultrasound. Application of high energy ultrasound to a small area may avoid excessive pain and provide optimal conditions for transdermal analyte extraction or drug delivery.

Geometric Channeling

High energies of ultrasound at a small area of the skin surface can be achieved by geometrically confining the ultrasound beam to a small area. Disclosed herein are methods and devices for channeling ultrasound energy by geometrically confining an ultrasound beam into a narrow region for the purpose of transdermal analyte extraction or drug delivery.

The ultrasound beam can be channeled or focused using an appropriately designed transducer such as a concave transducer or a phased array of transducers. Alternatively, the beam can be focused onto a small area using a chamber having walls that channel the beam. These methods create a localized erosion on the skin in order to interrupt the integrity of the skin.

FIG. 1 illustrates a schematic of a device 10 for sonophoretic analyte extraction or drug delivery using focused or channeled ultrasound. The device includes an ultrasound delivery chamber 12 that contains the ultrasound transducer and channeling means and is connected to an electrical signal generator and amplifier 14 which provides the driving and controlling mechanism for the transducer. The device may include a vacuum pump 16 and current generator 18, for purposes described below.

Figure 2:
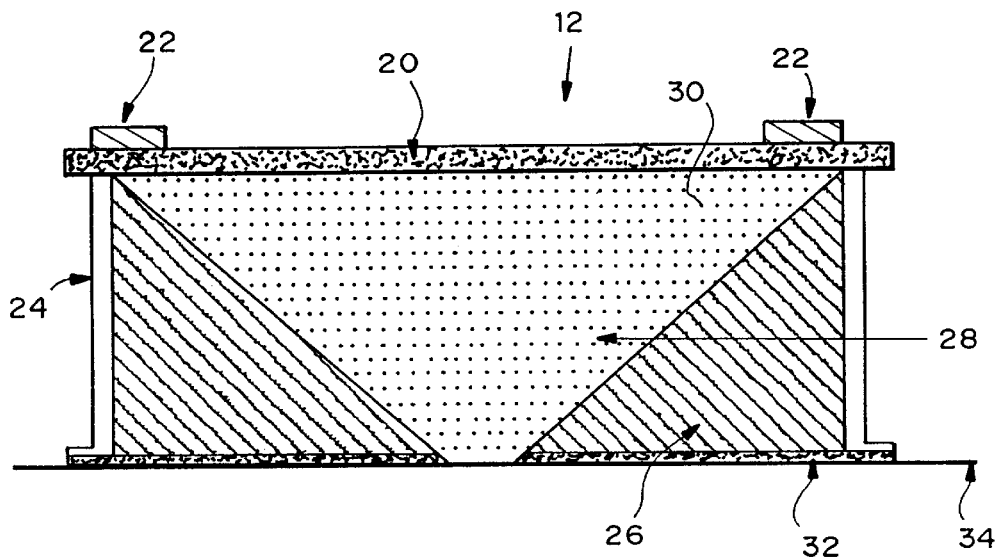
FIG. 2 is a side elevational view of one embodiment of an ultrasound channeling chamber having cone shaped channelling walls.

A first embodiment of a chamber 12 is shown in FIG. 2. The ultrasound transducer 20 in the chamber is connected to the electrical signal generator and amplifier (not shown) through electrical contacts 22. The chamber 12 includes exterior walls 24 made from polymer or metal. The interior walls 26, made from a material that reflects rather than absorbs acoustic energy such as plexiglass or other non-deforming material such as metal, are shaped to define a cavity 28 having the shape of a truncated cone with a large opening and a small opening. The cavity is preferably filled with a coupling medium 30 which transmits ultrasound, preferably transmitting sound in a manner equivalent to or better than air. The interior surface of the walls facing the cavity may be lined with an ultrasound reflecting medium such as a metal, polymer, or ceramic material. Metals such as aluminum may be preferred due to their high heat conductivity which may minimize temperature increase upon ultrasound application. An adhesive layer 32 on the bottom of the chamber is used to attach the chamber to the skin 34.

Figure 3:
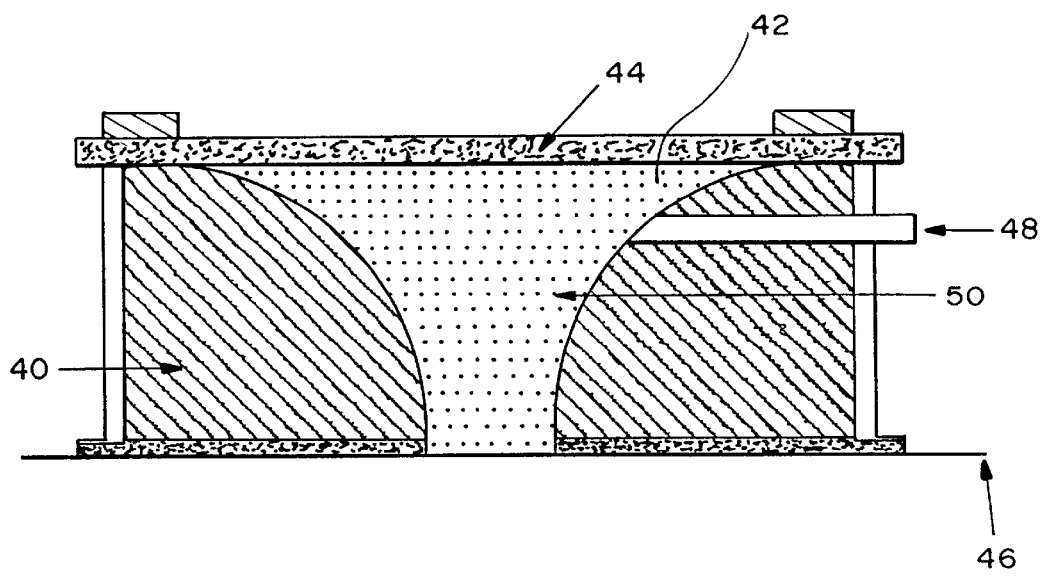
FIG. 3 is a side elevational view of a second embodiment of an ultrasound channeling chamber having horn shaped channelling walls.
Figure 4:
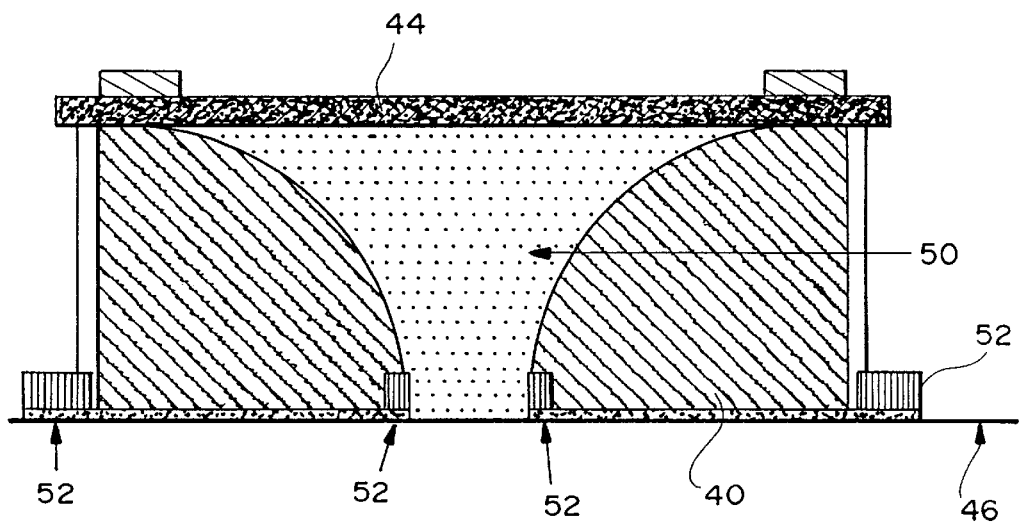
FIG. 4 is a side elevational view of the ultrasound channeling chamber of FIG. 3 including electrodes for application of an electric field.

A second embodiment of a chamber is illustrated in FIG. 3. In this embodiment, the interior walls 40 define a cavity 42 that is horn shaped, wherein the larger opening is towards the transducer 44 and the smaller opening is towards the skin 46. The chamber is optionally connected to a vacuum pump through a port 48 which opens into the coupling medium 50. FIG. 4 illustrates another optional aspect of the chambers, wherein the chamber optionally includes a pair of electrodes 52 for application of electric current to the skin as an additional mechanism for transport enhancement. The necessary current is provided by a current generator (see FIG. 1).

The Transducer

The ultrasound transducer is located at the larger end of the cone or the horn. The transducer may be either a piezo, ceramic or polymer block. The transducer may be machined from a single block of appropriate material or may be built by gluing multiple sheets of corresponding material. The focal diameter of the ultrasound beam before it is channeled may be between several millimeters to several centimeters. Ultrasound energy is localized at the small opening of the chamber due to channeling of the ultrasound beam. The second diameter of the beam is between about one μm to two cm, preferably between about 0.1 mm to one cm. The acoustic energy should not decrease more than 50%, preferably not more than 10%, as it is channelled. The decrease will, of course, be limited by the material and construction of the interior walls.

The transducer may be operated at a frequency in the range of between 20 kHz and 2 MHz using appropriate electrical signal generators and amplifiers. The transducer preferably is operated at a frequency in the range of between 20 and 200 kHz. Other ultrasound parameters including, but not limited to, amplitude, duty cycle, distance from the skin, and application time may be varied to achieve sufficient enhancement of transdermal transport. The pressure amplitude may be varied from above zero to 50 kPa. The duty cycle can vary from between one and 100%. The transducer can be positioned at a distance from the skin between 0.5 and 10 mm. The application time can range between 20 seconds and two minutes.

Figure 5:
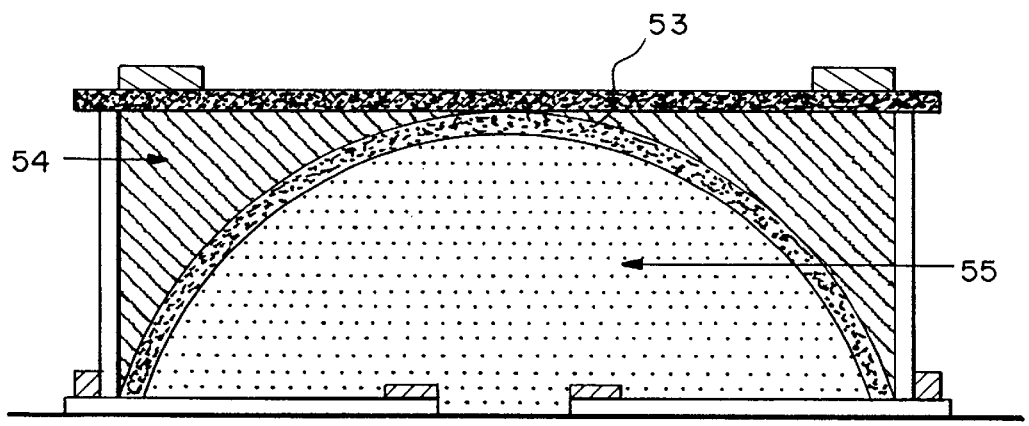
FIG. 5 is a side elevational view of a third embodiment of an ultrasound channeling chamber having a hemi-spherical transducer.

A third embodiment of a channeling or focusing chamber is illustrated in FIG. 5, wherein the transducer 53 is hemispherical shaped and defines the cavity 55. Backing material 54 provides support for and insulation for the transducer 53. The transducer may be a hemispherical shell as shown in FIG. 5 or it may be a solid piece with a hemispherical shaped depression. In other words, the transducer could be shaped like the transducer plus backing material (as shown in FIG. 5). The radius of curvature of the transducer is designed to focus the beam to an area of about 0.1 mm to one cm in diameter on the skin surface. The cavity 55 should preferably contain coupling media.

Figure 6:
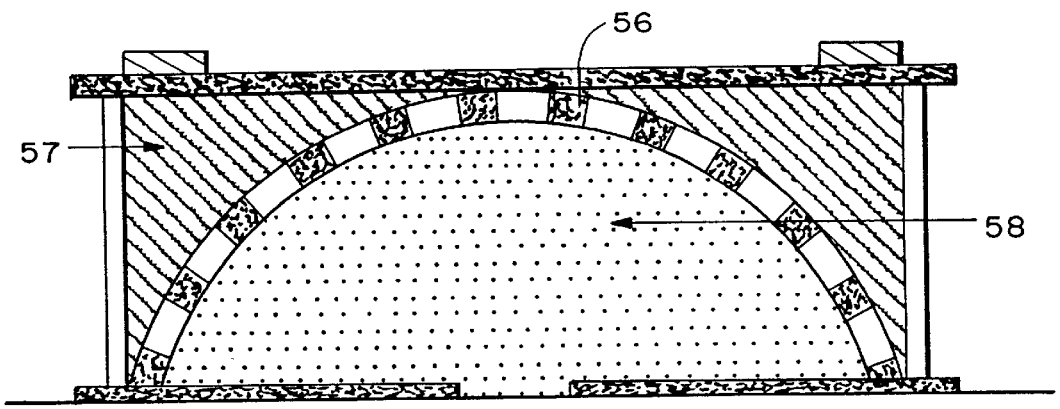
FIG. 6 is a side elevational view of a fourth embodiment of an ultrasound channeling chamber having an array of transducers arranged hemi-spherically.

Focused ultrasound may also be achieved by using a phased array of transducers as shown in FIG. 6. This array consists of multiple individual transducers 56 arranged to form a hemispherical wall. Each transducer of the phased array is individually activated using signal generators and amplifiers. This embodiment also includes backing material 57 and coupling medium 58.

The parameters of the transducer are as described above for the embodiments of FIGS. 1 through 4. The embodiments illustrated by FIGS. 5 and 6 may also include vacuum means and means to apply electric current or other physical enhancers.

Coupling Medium

The cavity may be filled with an aqueous or non-aqueous coupling medium including, but not limited to, water, saline, alcohols including ethanol and isopropanol (in a concentration range of 10 to 100% in aqueous solution), surfactants such as Triton X-100 or Sodium Dodecyl Sulfate (preferably in a concentration range of between 0.001 and 10% in aqueous solution), DMSO (preferably in a concentration range of between 10 and 100% in aqueous solution), fatty acids such as linoleic acid (preferably in a concentration range of between 0.1 and two % in ethanol-water (50:50) mixture), azone (preferably in a concentration range of between 0.1 and 10% in ethanol-water (50:50) mixture), polyethylene glycol in a concentration range of preferably between 0.1 and 50% in aqueous solution, histamine in a concentration range of preferably between 0.1 and 100 mg/ml in aqueous solution, EDTA in a concentration range of preferably between one and 100 mM, sodium hydroxide in a concentration range of preferably between one and 100 mM, and combinations thereof.

In the case of drug delivery, the coupling medium also contains a drug that is transported across the skin by diffusion or other driving forces including convection and iontophoresis.

The coupling medium increases the efficient transfer of ultrasound energy from transducer to the skin. Appropriate mixtures of these coupling media may also enhance cavitation activity near the skin or inside the skin, increasing effectiveness of transport of molecules across the skin. Experiments have shown that cavitation can be affected by the coupling medium. Physico-chemical attributes of the medium such as vapor pressure and surface tension influence the degree of cavitation of the medium. Cavitation can also be enhanced by providing nuclei in the form of gas bubbles, crevices, or particulates such as titanium dioxide particles or polymer particles.

Occurrence of cavitation on the skin surface may also be enhanced by coating the skin surface with a wetting agent in the entire area of application of ultrasound except for a spot. Cavitation may preferentially occur at the spot due to the difference in wetting properties of the skin and the coating. The coating may be made from a polymer such as poly (methyl methacrylate) or it may be a membrane made from poly(vinyl difluoride), for example.

Transport enhancement may be obtained by adding capillary permeability enhancers, for example, histamine, to the coupling medium. The concentration of histamine in the coupling medium may be in the range of between 0.1 and 100 mg/ml. These agents may be delivered across the epidermis during application of ultrasound and may cause local edema which increases local fluid pressure and may enhance transport of analytes across the skin. In addition, the occurrence of free fluid due to edema may induce cavitation locally so as to enhance transport of analytes as well as drugs across the skin.

Ultrasound Vibrating Element

Devices and methods are described herein using a vibrating element such as a needle or wire for the purpose of enhancing transdermal analyte extraction or drug delivery. In one embodiment, the element is in a transverse mode where the element is vibrating perpendicular to its long axis. In various embodiments, the element can be positioned above the skin, just touching the skin, or penetrating the skin. In one embodiment, the element is allowed to oscillate on the skin to make a hole or abraded area on the skin and, as oscillation continues, facilitates pumping of interstitial fluid or blood out of the body. Alternatively, the element can be used to enhance drug delivery.

The vibrating element can be used with or without coupling media. An advantage of not using coupling media, particularly in connection to analyte extraction and assay, is that complications of dilution are avoided. In other words, a change in volume does not have to be calculated in determining analyte concentration in the extracted blood or interstitial fluid. If the element is just touching or penetrates the skin, coupling medium is not necessary.

Another advantage of using coupling media is that acoustic streaming may result. The application of ultrasound in fluids is known to produce convective flow, a condition termed acoustic streaming. Streaming velocities are highest near the ultrasound source. This streaming can alter biological tissue, causing cell distortion and lysis or producing convective flow patterns inside tissue and cells. When acoustic streaming occurs over an existing hole in the skin, drug delivery can be facilitated by the convective flow of drug-containing fluid into the hole or the extraction of clinically relevant analytes can be facilitated through the convective flow of interstitial fluid or blood out of the hole.

Moreover, cavitation, mechanical oscillations of the skin, and local shearing forces may be increased using an appropriate coupling medium and may further enhance transdermal transport.

The pain receptors of the skin are present in the dermis but not the outermost layers of the skin, the epidermis and stratum corneum. Thus the epidermis and stratum corneum may be penetrated or small areas removed with little or no sensation. The outer layers of skin can be abraded through the use of a vibrating element, causing a break in the skin integrity. Alternatively, a needle penetrating only the outer most layers of the skin can create a very small hole (from about 50 μm to one mm in diameter) through which blood or interstitial fluid can be collected from the dermis without pain. The element can also produce acoustic streaming which may enhance the flow of fluid from the hole, resulting in the collection of fluid volumes which are practical for analysis. The enhanced fluid flow allows the extraction of blood from sites that are less vascularized and less innervated than the finger tips, such as, for example, the wrist or forearm. Thus a measurement can be taken at a site where pain is much less likely to occur as well as from a fingertip without pain.

The use of a vibrating element to pump fluid into or out of a hole in the skin presents at least three distinct advantages. More fluid flows through the skin: either analyte out of the hole or drug into the hole. The effect of ultrasound is localized allowing ultrasound to be delivered at higher intensities without significant pain or discomfort. Moreover, the penetrating depth of the element can be limited to only the stratum corneum and epidermis, thus allowing blood or interstitial fluid to be collected with little stimulation to the pain receptors in the dermis. Ultrasound transducers are known to rapidly heat under continuous operation, reaching temperatures that can cause skin damage. Heat damage to the skin can be eliminated by using a transducer that is located away from the skin to oscillate a small element near the skin. Moreover, because the element is small and does not heat, it can be located near the hole. Thus, the hole is exposed to the region of greatest fluid velocity, resulting in greater pumping efficiency.

The vibrating element may penetrate into the skin (up to about 150 μm) constantly or intermittently due to ultrasonic vibrations and erode the epidermis in that area. Alternatively, the vibrating element may not penetrate the skin and may enhance transport by making skin more permeable. Interstitial fluid or blood in the punctured or eroded area may then be collected in the element or in the coupling medium by application of vacuum, by diffusion, or by capillary action. If the vibrating element does not touch or penetrate the skin, coupling media should be used during application of the ultrasound. The coupling media can be removed prior to collection of the analyte to avoid dilution.

Figure 7:
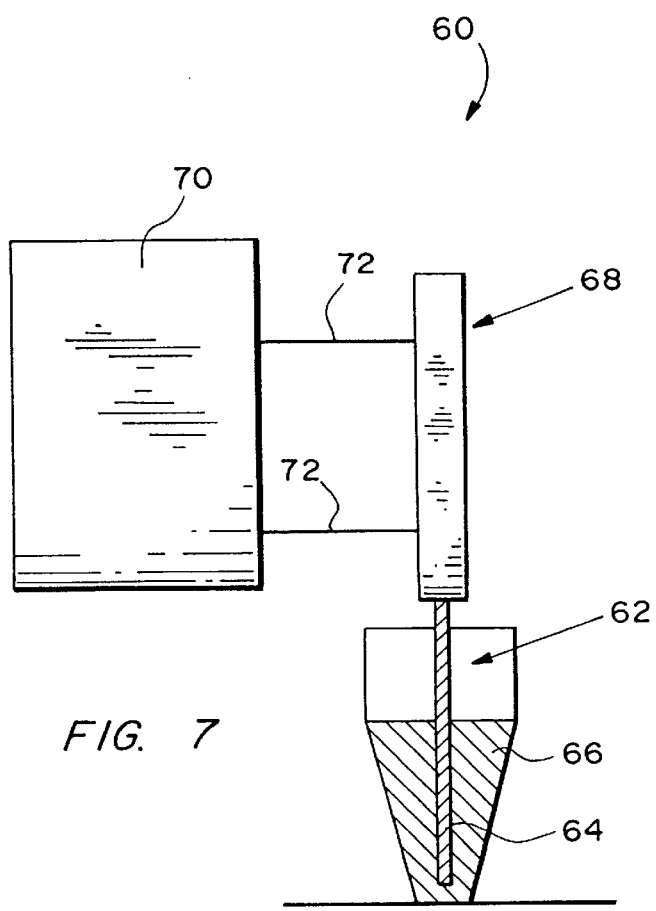
FIG. 7 is a side elevational view of a device for application of ultrasound through a vibrating element.

FIG. 7 illustrates one embodiment of a device 60 for analyte extraction or drug delivery using a vibrating element positioned above the skin surface. The device includes a chamber 62 containing the vibrating element 64 and a coupling medium 66 such as those described above for the geometric ultrasound focusing devices. The element is fixed at one end to a piezoelectric transducer, magnetostritive transducer, or other vibration producing device 68. Piezoelectric transducers that produce large displacements such as Bimorph transducers and stacked piezoelectric transducers are preferred. Vibrations produced by the transducer 68 are translated to the element which oscillates, preferably in the transverse mode.

Oscillations are produced using an alternating voltage generator coupled to a power amplifier. The voltage wave form is preferably sinusoidal. The ultrasound producing system consisting of the element, transducer, voltage generator and power amplifier, may be powered by standard household power or through a battery. The ultrasound transducer 68 is connected to electrical signal generator and amplifier 70 through electrical contacts 72.

The vibrating element may be fabricated with a channel in the center to provide means for collection of the blood or interstitial fluid or delivery of drug. Alternatively, the analyte may be collected, or the drug delivered from, the chamber.

Figure 9:
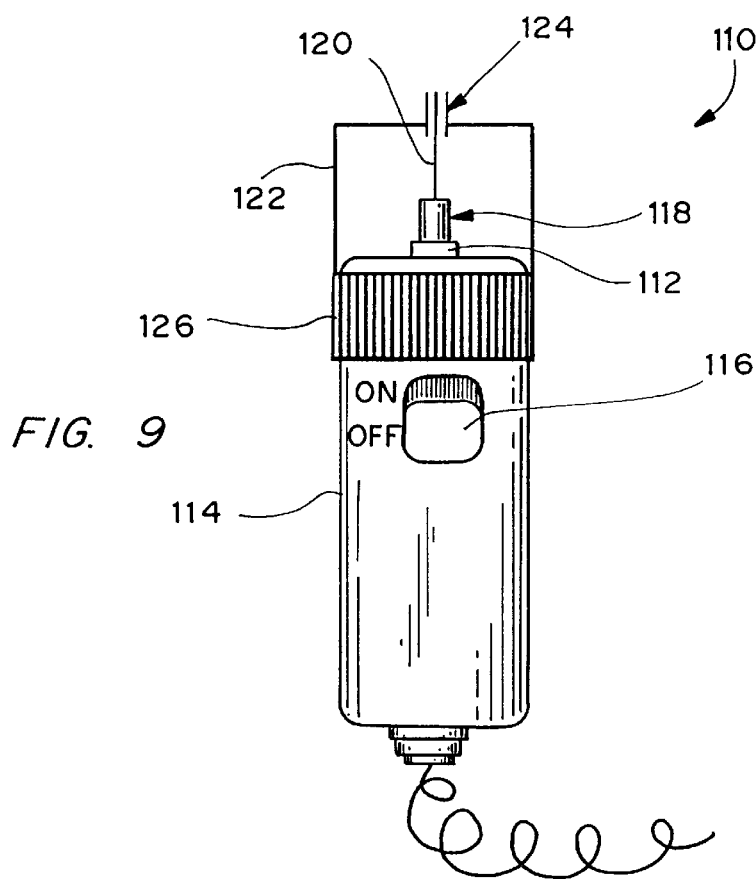
FIG. 9 is a side elevational view of another device for application of ultrasound through a vibrating element.

FIG. 9 illustrates an embodiment of a device 110 for application of ultrasound through a vibrating element that is positioned just touching the skin surface or that penetrates the skin. A shaft 112 is connected to vibration producing means (not shown) located in enclosure 114. The vibration producing means may operate by mechanical, electrical, electromechanical, or ultrasonic means. Vibration of the element may be transverse, that is, perpendicular to the skin, parallel to the skin, or at an angle. The device 110 is operated by a rechargeable battery and operated by means of switch 116. The vibration frequency applied to the element varies from about 1 kHz to 100 kHz. The magnitude of vibration of the shaft varies from about one μm to five mm.

Shaft 112 is connected to element holder 118 which retains element 120 and may lock element 120 in place. Element 120 may be a needle. Cap 122, optionally including capillary tube 124, has a hole through which element 120 protrudes. The diameter of the hole varies from about 10 μm to five mm and determines the magnitude of vibration of the element tip. The length of the element protruding may be controlled from about zero to 500 μm using screw control 126. A longer protrusion is needed when using the device on a fingertip due to thicker epidermis in that area of skin as compared to the wrist, for example. Moreover, the device can be used so that the element does not penetrate the skin.

To use, the person places the device on the desired area of skin and turns the device on for between five seconds and two minutes. Surface blood resulting from application of the device may be squeezed onto a collection strip or drawn up through the capillary tube 124 and collected for assay.

Figure 10:
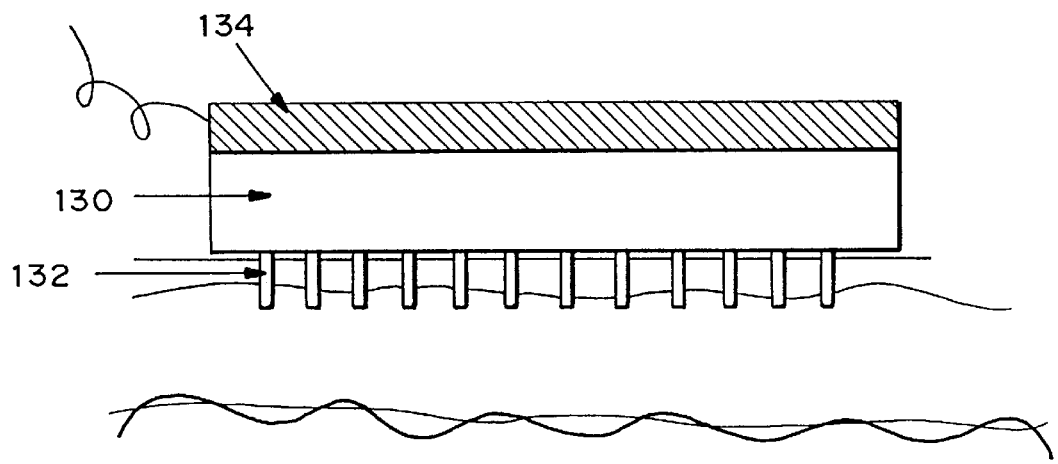
FIG. 10 is a side elevational view of a device for application of ultrasound through a plurality of vibrating elements.

The device illustrated in FIG. 10 demonstrates the use of a plurality of vibrating elements. The device includes reservoir 130 for storage of drug to be delivered or analyte to be collected. One or more elements 132, which may be hollow microneedles, extend from the reservoir and have a length so that they may extend into the SC but not beyond the epidermis when the device is placed against the skin. Alternatively, the elements may be positioned to just contact the skin. The device is equipped with a transducer 134 for application of ultrasound to the elements. Alternatively, or in addition, the device may be provided with means for applying an electric current or other physical enhancer across the elements.

The Element

The element may be cylindrical in shape for each of the embodiments discussed. It may possess a conical tip, hemispherical tip or have any other geometry suitable for contacting the skin without puncturing the skin or for creating a small hole in the skin. It may be made from stainless steel, tungsten or any other material possessing adequate tensile and fatigue strengths. It is preferred that the element is fabricated from a material with a high tensile strength (greater than 150 ksi). Examples of such materials include music wire (a high carbon steel alloy), hard drawn MB steels, oil tempered MB steels, chromium-vanadium steels, and spring brass.

The element can be of any practical length and from between about 10 $\mu$m and two cm, preferably between about 100 $\mu$m to 500 $\mu$m in diameter.

The distance of the vibrating element into or from the skin is important to create a small hole or abrasion in the skin and generate adequate acoustic streaming, if coupling media is not used. The unit may possess a subunit for controlling the distance of the element from the skin at between about 0.1 and 5 mm or the depth of the vibrating element into the skin in the range of up to about 150 $\mu$m. The subunit may alternatively position the element to where it touches the skin and impresses the skin without puncturing the skin. The element may puncture the skin after it begins to oscillate. The unit may also possess a subunit, which may be the same subunit, to control the downward force the needle exerts on the skin. This depth and/or force controlling subunit may be a cantilever beam on which the transducer and vibrating element are fixed.

It is preferred, to maximize oscillations at the tip of the element, to have the length of the element equal to odd multiples of the ultrasound wavelength divided by four. The deflection at the tip can also be modified by changing the stiffness of the element, with stiffer materials such as tungsten or 304 stainless steel resulting in smaller deflections than a more flexible material such as copper or music wire. The geometry of the tip of the element can be modified to produce different forces and flow patterns near the surface of the skin. A pointed tip will result in highly localized shearing forces and acoustic streaming near it while a blunt tip will produce more dispersed forces. These forces, and thus transdermal transport enhancement, can also be distributed by using arrays of elements mounted on transducer(s). The vibrating element is located near the skin hole to maximize the pumping action of acoustic streaming.

The element may be driven at a frequency in the range of between one kHz and 100 kHz, preferably between about 5 kHz and 100 kHz, using appropriate piezoelectric or magnetostritive transducers or equivalent means, electrical signal generators, and amplifiers. Other parameters including displacement amplitude of the transducer, duty cycle, distance from or into the skin, and application time may be varied to achieve skin penetration and sufficient enhancement of transdermal fluid extraction. The transducer displacement amplitude can range from about 5 to 100 $\mu$m. The duty cycle can vary from about 10 to 100%. The distance into the skin can range from about one to 150 $\mu$m. The application time can range from about 20 to 120 seconds. The physical dimensions and mechanical properties of the element can also be varied to enhanced transdermal fluid transport. For embodiments where the element does not contact or enter the skin, the element is preferably at between about 0.1 and five mm from the skin.

Sensor

Figure 8:
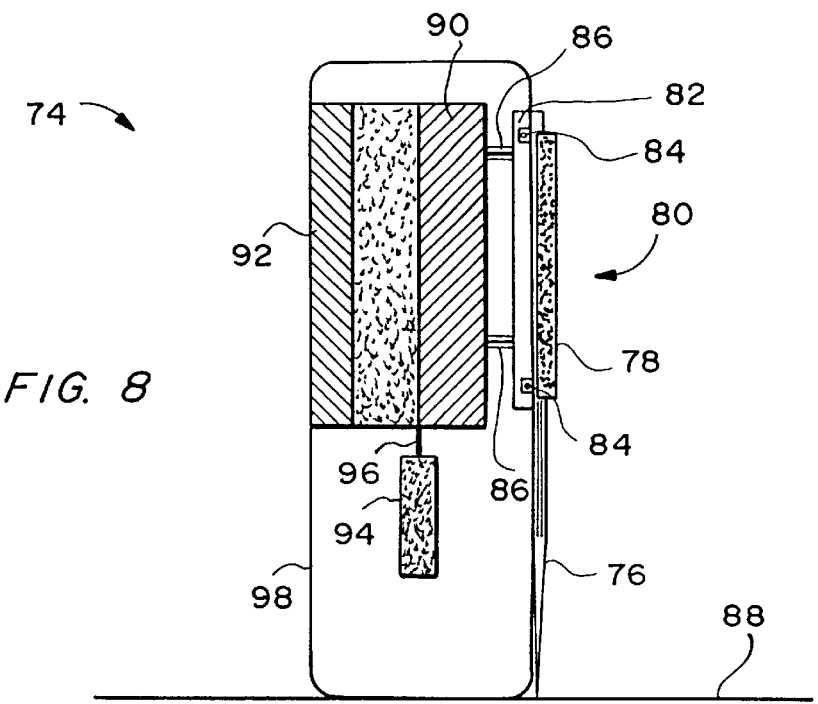
FIG. 8 is a side elevational view of a device for application of ultrasound through a vibrating element incorporated with a sensor for sensing an analyte.

The vibrating element may be integrated with a sensor, such as a chemical sensor, biosensor, or other measurement system to form a complete extraction/measurement system 74, as illustrated in FIG. 8. An element having an internal channel for fluid transfer is fabricated together with a sensor 78 to form a disposable unit 80 which is connected to the transducer 82 by connectors 84. The connectors may also establish electrical contact with the sensor if necessary. The transducer is mounted onto two cantilever beams 86 that control the force the element exerts on the skin 88 and the depth of penetration. Electrical leads are fabricated on the beams to establish electrical contact between the transducer 82 and its controller 90, and between the sensor 78 and the measurement electronics. The controller 90 may include an electrical function generator and a power amplifier.

A display 92 shows the measured analyte concentration to the user. The entire system is powered by a battery 94 which is connected to all electronics by electrical leads 96. The system is encased in a housing 98 to protect the electronics. The housing also serves as a stop to prevent the needle from penetrating too deeply into the skin when the device is placed upon the skin.

The vibrating element 76 is fabricated with a channel in its center to provide space for the collection of blood or interstitial fluid. The channel may be lined with a coating such as borosilicate glass or silicon dioxide to facilitate the capillary flow of fluid. The vibrating element with integrated channel may be produced by silicon micromachining.

The system operates by fastening the disposable unit 80 to the transducer 82 and placing the housing 98 against the skin 88. The system is then activated and the extracted fluid is transferred through the element's channel to the sensor. The analyte of interest is measured and the reading displayed to the user. The system is automatically deactivated and the user discards the disposable unit.

The sensing system may be in direct contact with the coupling media or the coupling media may be transferred to the sensor. Transfer may occur by wicking with an absorbent material, by capillary action, by electroosmotic flow, or by pumping including ultrasound pumping.

The unit can be constructed to function as a closed loop drug delivery unit, including drug delivery means, analyte recovery means, sensing means to measure the analyte, and control means to provide a signal to the drug delivery means. In a preferred embodiment, the unit would include subunits to withdraw fluid and calculate the concentration of glucose therewithin, determine the amount of insulin needed, and deliver that amount of insulin.

Figure 11:
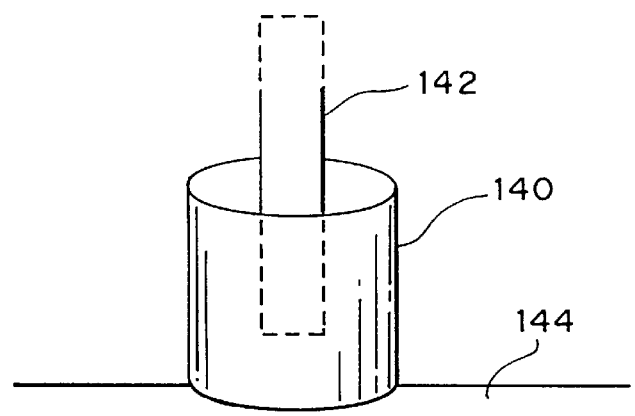
FIG. 11 is a perspective view of a noninvasive ultrasound application device.

Another noninvasive technique, illustrated by FIG. 11, is useful for analyte extraction. The technique is described as an exemplary embodiment but it should be realized that many changes can be made from the parameters and device described herein. The technique employs a chamber 140 and an ultrasound probe 142. The chamber may have a variety of shapes but is cylindrical in the exemplary embodiment, with open ends, about 1.5 cm$^2$ in area. One open end of the chamber is placed against the skin 144 at the desired location. Saline (about one ml) may be placed in the chamber for a period of time from above zero minutes to about one hour in order to hydrate the skin. The saline is then replaced with coupling media, which can be one of those described above and may include permeation enhancers. In the exemplary embodiment the coupling medium is one % sodium lauryl sulfate (SLS) in saline. An ultrasound transducer probe, cylindrical in shape, having a diameter of one cm is inserted into the chamber with the tip about one cm from the skin. The transducer was operated at about 20 kHz at a maximum pressure amplitude of 30 kPa (300 mW/cm$^2$ intensity), 50% duty cycle (five seconds on/five seconds off) for up to five minutes.

A second chamber filled with saline may be placed on the subject's arm in order to measure trans cutaneous conductivity at two frequencies, 10 Hz and one kHz. Ultrasound application was stopped when the skin conductance at 10 Hz and one kHz become comparable (within 20%). After this, the solution is removed from the chamber and replaced with 500 µl saline.

Vacuum (about 10 in Hg) is applied to the chamber for five minutes to extract fluid. The solution can then be assayed.

This technique was employed in assaying glucose from humans. In the first step, the transducer was operated at 11% amplitude, five seconds on/five seconds off, for one minute. In the second, analyte extraction step, vacuum was applied at 10 in Hg for five minutes. Glucose fluxes of from about 100 to 350 nmoles per cm$^2$ per hour were obtained. Glucose levels in blood were measured simultaneously and were comparable to the levels sen in the technique described herein. In addition, no pain or discomfort was reported and there was no damage or erythema to the site exposed to ultrasound.

The noninvasive technique was also tested on rats under similar conditions. Similar results were obtained. In the analyte extraction step, the transducer was operated at one % amplitude, five seconds on/five seconds off, for 15 minutes. Glucose fluxes of 150 nmoles per cm$^2$ per hour were obtained and blood glucose levels of 100 mg/dl. These fluxes are 70 times higher than those obtained using reverse iontophoresis.

Other transport enhancement methods could be used instead of, or in addition to, vacuum. For example, other transdermal transport driving forces include osmotic pressure gradient, electric current, ultrasound under different conditions, electroporation, magnetic fields, and mechanical pressure.

This two step method could be used as well for drug delivery. The skin would be made permeable by application of ultrasound followed by the application of drug to the skin and transport of the drug either by diffusion or with the help of a physical enhancer.

Practical Application

Practical operation of a sonophoretic analyte monitoring device is conceived as follows. The patient unpacks a disposable unit and inserts it into a portable or bench-top ultrasound generator. The ultrasound generator may also include circuitry for skin resistance or hemoglobin measurements, analyte concentration measurements, and display of the measured analyte concentration. The entire system (sonicator and disposable unit) is placed against the skin and ultrasound is activated for a certain period of time either alone or along with other physico-chemical fields including chemicals, electric field, vacuum, and pressure fields. The extracted analytes from the skin are collected in the disposable unit and are measured using appropriate assays. A similar operation may be used for drug delivery where the patient unpacks a disposable containing drug and loads it into an ultrasound generating device. The entire assembly is placed against the skin and the device is activated.

Alternatively, the sensing element could be located elsewhere and the contents of the chamber in contact with skin and exposed to ultrasound can be pumped using mechanical forces, capillary forces, ultrasound, vacuum, or electroosmotic forces into the sensing chamber and analyzed for the analyte of interest.

The chamber also may contain two or four electrodes for skin conductance measurement. Measurements of skin conductance may be required to minimize variations of the analyte flux from patient to patient or from site to site within the same patient. These measurements are performed by applying a small AC or DC electric potential across two electrically isolated electrodes in contact with skin. The electric current flowing through these electrodes is measured using an ammeter and the skin resistance is measured using the values of the potential and the current.

Assay of Analyte

The ultrasound is applied to the skin at the site where the sample is to be collected. A reservoir or collecting container is applied to the site for collection of the sample, which is then measured using standard techniques. The ultrasound conditions are optimized as in the case for drug delivery, to maximize analyte recovery, while maintaining the relative levels of the analyte to other components of the sample.

In the case of analyte extraction using either of the above-described means of focusing ultrasound, the amount of analyte extracted in the coupling medium is measured using appropriate assay methods. For example, an assay method which results in a color change could be used. The change in color could be detected using a light beam which enters into the disposable chamber through a window on top. The analyte may also be detected in the chamber through the use of an enzyme electrode or biosensor. An example of an enzyme electrode for glucose is a screen-printed electrode on the surface of which is immobilized glucose oxidase and an electron mediator such as ferrocene or its derivatives. Electrons generated by the oxidation of glucose are transferred from glucose oxidase to the electrode via the mediator. Thus, the concentration of glucose in the analyte solution is proportional to the current generated. Yet another detection mechanism may be used based on near-infrared spectroscopy. In this method, concentration of extracted glucose in the gel is detected by the absorption of the near-infrared light which passes through the chamber through two windows. The window through which the light passes may be separate from the ultrasound transducer or the beam may pass directly through the transducer.

In other words, the analyte sensing system may consist of enzymes that react with the analyte of interest and either electrochemical or optical transducers that measure the content of reaction. Examples of such enzymes include but are not limited to glucose oxidase and glucose dehydrogenase. Using glucose oxidase as an example, glucose is measured using either of the following reactions: glucose+$O_2 \rightarrow$ gluconolactone+$H_2O_2$; glucose+$2M_O \rightarrow$gluconolactone+$2M_R$ where M is a mediator in its oxidized (O) or reduced (R) state. An electrochemical transducer then measures either the consumption of $O_2$, $M_O$ or the production of $H_2O_2$ or $M_R$. Examples of mediators (M) include, but are not limited to, ferrocene and its derivatives or polymers containing Os (bis-bipyridine)$_2$Cl. The electrochemical transducer may consist of a two or three electrode system, with the electrode materials being gold, silver, silver/silver chloride, platinum, palladium or carbon. Electrode potentials are controlled by and electrochemical reactions monitored by a potentiostat.

Optical transducers monitor the disappearance of $M_O$ or the appearance of $M_R$. The optical transducer consists of a light source which may be mono- or polychromatic and may be a light-emitting diode or an optical fiber. In addition to the light source, the optical transducer contains a device to measure the transmittance or absorbance change produced by the enzymatic reaction. This device may be, but is not limited to, a photodiode.

The chamber may also contain mechanisms for measuring concentrations of more than one analyte for the purpose of minimizing variability in fluxes of extracted analytes. For example, measurement of the amount of ions extracted during sonophoresis could be used as a normalization factor for the variations in the amount of glucose extracted during the same period of time. This may be achieved by measuring conductivity in the extraction fluid or measuring individual ions using ion-selective electrodes. Ion concentration may also be used to control the application of ultrasound. When ion concentration reaches a predetermined level, ultrasound is turned off.

If blood is withdrawn, normalization may be achieved by measuring the amount of hemoglobin in the extraction solution. Hemoglobin, having a relatively constant concentration in blood, will provide a measure of the volume of blood extracted. Hemoglobin may be measured spectroscopically at a wavelength of 540 nm. Hemoglobin concentration may also be used to control the application of ultrasound. When hemoglobin concentration reaches a predetermined level, ultrasound is turned off.

In addition to a primary analyte, secondary analytes are also extracted. The concentration of the primary analyte can be normalized, lowering extraction to extraction and site to site variability, by the concentration of the secondary analyte. Examples of the secondary analyte include, but are not limited to, salts, creatinine, cholesterol and triglycerides. Measurements of salts include specific ion measurements such as $Na^+$ or $Ca^{2+}$ or overall ion-measurements using solution conductivity. Normalization may be a linear or non-linear relationship.

Administration of Drug

The drug is preferably administered to the skin at a site selected based on convenience to the patient as well as maximum drug penetration. For example, the arm, thigh, or stomach represent areas of relatively thin skin and high surface area, while the hands and feet are uneven and calloused. In the preferred embodiment, drug is applied to the site and ultrasound applied immediately thereafter. Alternatively, ultrasound could be applied first to increase the permeability of the skin and then drug applied to the site where it diffuses through the skin or is otherwise transported through the skin.

Based on these calculations and the data in the following examples, one can calculate the required dosage and application regime for treatment of a patient, as follows. A typical diabetic patient (70 Kg weight) takes about 12 Units of insulin three times a day (total dose of about 36 Units per day: cited in 'World Book of Diabetes in Practice' Krall, L. P. (Ed), Elsvier, 1988). If each insulin dose was to be delivered by sonophoresis in one hour, the required transdermal flux would be 12 U/hour. Note that one unit (one U) of insulin corresponds approximately to 40 mg of insulin. The transdermal patch area used in these calculations is 40 $cm^2$ (the area of a transdermal Fentanyl™ patch [ALZA Corporation]). The donor concentrations used in these calculations are 100 U/ml in the case of insulin (commercially available insulin solution [Humulin™]), $3 \times 10^7$ in the case of γ-interferon (typical concentration of interferon solution recommended by Genzyme Corporation), and $3 \times 10^5$ U/ml in the case of erythropoeitin [Davis J., Arakawa T., Strickland T., Yphantis D., Biochemistry, 2633–2638, 1987].

A typical γ-interferon dose given each time to patients suffering from cancer or viral infections is about $5 \times 10^6$ U (Grups J. W., Frohmuller H. G., Br. J. Med., 1989, 64 (3) 218–220; Parkin J. M., Eales L., Galazka A., Pinching A., Br. Med. J., 1987, 294: 1185–1186) Similar doses of α-interferon and β-interferon have also been shown to enhance the immune response of patients suffering from viral infections and cancer (cited in 'Clinical Applications of interferons and their inducers', Ed. Stringfellow D., Marcel Dekker, New York, 1986). If this interferon dose was to be given by sonophoresis in one hour, the required transdermal flux would be $5 \times 10^6$ U/hour. Note that one unit of γ-interferon corresponds approximately to one pg of γ-interferon.

A typical daily erythropoeitin dose given subcutaneously to anemic patients is about 400 U (cited in 'Subcutaneous Erythropoeitin, Bommer J., Ritz E., Weinreich T., Bommer G., Ziegler T., Lancet, 406, 1988). If this dose was to be delivered in three steps, each involving sonophoresis for one hour, the transdermal flux required would be about 140 U/hour. Note that one unit of erythropoeitin corresponds approximately to 7.6 nanograms of erythropoeitin.

Physical and Chemical Enhancers

Physical and chemical enhancers can be used in combination with the ultrasound devices and methods described herein. Physical enhancers, as used herein, include suction (see FIG. 4), osmotic pressure gradient, iontophoresis, electroporation, magnetic fields, and mechanical pressure. Ultrasound is used to permeabilize the skin followed by the application of various force fields to provide additional driving force for transdermal transport of molecules. Application of suction may induce convective transport across the skin, thus enhancing the effect of ultrasound on transdermal transport. Application of osmotic gradient or electric current may also enhance transdermal transport by similar mechanisms. Necessary osmotic gradient may be provided using salts (for example, 2 M NaCl) or sugars such as mannitol (1 M solution in saline) and dextrans. The use of physical enhancers has been described elsewhere. Chemical enhancers described above may be used as well.

EXAMPLE ONE

Extraction of Blood and Measurement of Glucose

A device as illustrated in FIG. 7 was constructed as follows. The titanium tip of a VCX-400 ultrasound horn (Sonics & Materials, CT) was modified with a vibrating needle by drilling a hole in the tip perpendicular to the direction of transducer displacement and fixing a 24 mm long by one mm diameter needle into the hole using epoxy resin. A chamber with a 1.4 mm diameter orifice was placed against the skin and filed with 50 μl of 100 mM NaOH in isotonic saline which served as the coupling media. The site used was on the back of the hand. The needle was immersed in the coupling media with the tip of the needle approximately 0.2 mm from the skin. The horn was not in contact with the coupling media or chamber. Ultrasound was then applied continuous for a period of one minute. At the end of the exposure period, the coupling media was collected and the glucose concentration determined using high pressure liquid chromatography with pulsed amperometric detection. The extraction procedure was performed on 4 human volunteers with 5 repetitions at the same site. The results are summarized in Table 1.

TABLE 1

Transdermal Glucose Extraction from Human Volunteers: Glucose Concentration ($\mu$g/ml) in Extraction Fluid

| Extract Number | Subject 1 Site 1 | Subject 1 Site 2 | Subject 2 Site 1 | Subject 2 Site 2 | Subject 3 Site 1 | Subject 4 Site 1 |
|---|---|---|---|---|---|---|
| 1 | 2.4 | 1.4 | 1.8 | 1.1 | 3.5 | 0.62 |
| 2 | 1.5 | 0.89 | 1.1 | 1.8 | 2.3 | 0.57 |
| 3 | — | 1.0 | 1.2 | 1.2 | 2.5 | 0.40 |
| 4 | 0.74 | 0.86 | 0.97 | 2.9 | 1.9 | 0.45 |
| 5 | 1.8 | 0.72 | 1.6 | 1.7 | 2.9 | 0.56 |
| Average | 1.6 | 0.97 | 1.3 | 1.74 | 2.6 | 0.52 |
| RSD | 43% | 25% | 15% | 43% | 22% | 17% |

The amounts of glucose recovered and the standard deviation between the same subject are comparable to results obtained using reverse iontophoresis. However, the presently disclosed method took less time by a factor of 15.

EXAMPLE TWO
Extraction of Glucose with Vibrating Needle Element

In this case the same general approach was used, but in addition there was a mechanism to use the ultrasound element to puncture the skin, then it was removed and vibrated in the transverse mode to pump out more glucose than could be otherwise obtained. To demonstrate this concept, a sewing needle was used as the transverse oscillating element. The chamber shown in FIG. 7 was placed against the skin. The system was set up such that the oscillating needle could be lowered independent of the chamber. A micrometer was used to advance the needle until it penetrated the stratum corneum into the epidermis or further penetrated to the dermis, to extract interstitial fluid or blood, respectively. Then the micrometer was used to withdraw the needle so it was no longer touching, but was located just above the skin. Then the needle was made to oscillate, fluid was collected, and assayed. The results were comparable to Example 1.

EXAMPLE THREE
Extraction of Glucose with Vibrating Transverse Needle

In this case the oscillating element penetrated the skin. The oscillating element was an acupuncture needle that was attached in the transverse mode to a transducer. The acupuncture needle was inserted in the skin to a fixed depth using a micrometer as in the second example. The acupuncture needle was then oscillated as described above to help dissolve interstitial fluid from its gel-like consistency so it can be pumped out of the body and assayed. Deeper penetration of the acupuncture needle enables this technique to obtain blood samples. This system can be modified in such a way to maximize the interstitial fluid or blood obtained. One such modification is to make the acupuncture needle so that it has flanges that run its length that promote capillary forces to help extract fluid. Another modification is to use a frequency of oscillation, length of the acupuncture type needle and the depth to which it is placed in the skin such that oscillations are minimized at depths that result in pain and maximized at depths that promote fluid extraction using the fact that such an oscillating element will have nodes at which motion is minimal. The results were comparable to Example 1.

EXAMPLE FOUR
Extraction Using an Oscillating Needle

In this example, the element was positioned just touching the skin. A transverse oscillator was constructed using an acupuncture needle (Black Dragon 38 Gauge) mounted transversely at the end of an ultrasonic unit (VSX 400 Sonics and Materials) The acupuncture needle protruded 1.831 cm from the side of the horn. A sample well was constructed out of an HPLC insert vial, cut approximately in half. The diameter of the bottom of the well was about 2.45 mm.

The oscillating needle was lowered to be at the bottom of the sample well, as indicated by moving a finger under the well and seeing the needle move. By adjusting a lab clamp holding the sample well, the well was lowered the minimum amount such that the needle no longer moved when a fingertip was moved under the bottom of the sample well.

The back of the left hand was positioned in touch with the bottom of the well so fluid would not leak out. 20 microliters of distilled water were put in the well and the sample was sonicated for one minute, continuous power, at an amplitude of about 35%–36%. The sample was retrieved using another 40 microliters to wash out sample well and the samples were assayed using a standard HPLC procedure.

The results showed concentrations of glucose were obtained comparable to those obtained with Example 1. The average concentration obtained from five volunteers was 1.65 $\mu$g per ml. The average standard deviation was 1.16.

In another aspect, the devices and methods disclosed herein could utilize sound or ultrasound produced according to a phenomenon known as "Tartini tones", first described by Giuseppe Tartini, an 18th century Italian composer and described in an article by Larry Armstrong in the Dec. 2, 1996 issue of *Business Week*, pages 108–109. Lower frequencies (less than 10 kHz) can be produced using much smaller transducers. The method relies on the phenomenon that when two sound or ultrasound waves having different frequencies interact, a third wave is created, having a frequency intermediate between the two. The third wave can be focused.

We claim:

1. A device for application of ultrasound to the skin for enhancing transdermal transport, the device comprising an ultrasound transducer capable of emitting ultrasound at a frequency between 20 kHz and 2 MHz and walls forming a chamber for containing coupling medium,
   wherein the chamber is geometrically configured to direct the ultrasound to induce cavitation at the skin, when the chamber abuts the surface of the skin.

2. The device of claim 1, further comprising means for analyte recovery.

3. The device of claim 1, wherein the chamber walls form a truncated cone with a larger opening and a smaller opening and the transducer is located at the larger opening of the chamber.

4. The device of claim 1, wherein the chamber walls form a horn with a larger opening and a smaller opening and the transducer is located at the larger opening of the chamber.

5. The device of claim 1, wherein the ultrasound frequency which can be emitted by the device is between 20 kHz and 200 kHz.

6. The device of claim 1, further comprising means to apply an additional transdermal transport driving force selected from the group consisting of suction, osmotic pressure gradient, concentration gradient, iontophoresis, electroporation, magnetic field and mechanical pressure.

7. The device of claim 1, wherein the chamber walls are geometrically configured to create an abraded area on the skin having a diameter from about 100 $\mu$m to one cm.

8. The device of claim 1, wherein the transducer forms a part of the chamber walls.

9. The device of claim 1, wherein the chamber walls are made of a material selected from the group consisting of metal, polymer and ceramic.

10. The device of claim 1, wherein the transducer comprises a plurality of transducers.

11. A method of enhancing transdermal transport, comprising the steps:

providing an ultrasound device comprising an ultrasound transducer capable of emitting ultrasound at a frequency between 20 kHz and 2 MHz and walls forming a chamber for containing coupling medium, wherein the chamber is geometrically configured to direct the ultrasound to induce cavitation at the skin, when the chamber abuts the surface of the skin; and applying the directed ultrasound to an area of skin.

12. The method of claim 11 of effecting transdermal transport, comprising the steps:

applying ultrasound to an area of skin to make the skin more permeable;

removing the ultrasound; and applying a transdermal transport driving force selected from the group consisting of additional ultrasound, suction, osmotic pressure gradient, concentration gradient, iontophoresis, electroporation, magnetic field and mechanical pressure.

13. The method of claim 12 wherein the device includes a reservoir for collection of analyte, comprising the ultrasound to enhance analyte recovery.

14. The method of claim 12, wherein the ultrasound is applied by providing ultrasound having a frequency from about 20 kHz to 200 kHz.

15. The method of claim 12, wherein application of the directed ultrasound to the skin creates an abraded area on the skin having a diameter from about 100 $\mu$m to one cm.

* * * * *